United States Patent [19]
Brekke

[11] Patent Number: 5,981,825
[45] Date of Patent: Nov. 9, 1999

[54] DEVICE AND METHODS FOR IN VIVO CULTURING OF DIVERSE TISSUE CELLS

[75] Inventor: John H. Brekke, Duluth, Minn.

[73] Assignee: THM Biomedical, Inc., Duluth, Minn.

[21] Appl. No.: 08/242,557

[22] Filed: May 13, 1994

[51] Int. Cl.[6] .................................................. A61F 2/22
[52] U.S. Cl. .................................................... 623/11
[58] Field of Search ........................... 623/11, 16, 20; 435/240, 243, 240.2; 422/426

[56] References Cited

U.S. PATENT DOCUMENTS

| | | |
|---|---|---|
| 2,465,357 | 3/1949 | Correll ................................ 128/296 X |
| 2,610,625 | 9/1952 | Sifferd et al. ........................ 128/296 |
| 2,621,145 | 12/1952 | Sano . |
| 2,703,316 | 3/1955 | Schneider . |
| 2,758,987 | 8/1956 | Salzberg . |
| 3,463,158 | 8/1969 | Schmitt et al. . |
| 3,491,760 | 1/1970 | Braun et al. ........................ 128/335.5 |
| 3,636,956 | 1/1972 | Schneider ........................... 128/335.5 |
| 3,688,317 | 9/1972 | Kurtz ................................... 128/334 R |
| 3,739,773 | 6/1973 | Schmitt et al. ........................ 606/62 |
| 3,902,497 | 9/1975 | Casey . |
| 3,937,223 | 2/1976 | Roth ..................................... 128/296 |
| 4,164,560 | 8/1979 | Folkman et al. . |
| 4,181,983 | 1/1980 | Kulkarni . |
| 4,186,448 | 2/1980 | Brekke . |
| 4,279,249 | 7/1981 | Vert et al. . |
| 4,357,312 | 11/1982 | Hsieh et al. . |
| 4,419,340 | 12/1983 | Yolles . |
| 4,442,655 | 4/1984 | Stroetmann ............................ 623/16 |
| 4,505,266 | 3/1985 | Yannas et al. .......................... 623/15 |
| 4,553,272 | 11/1985 | Mears ..................................... 623/16 |
| 4,563,350 | 1/1986 | Nathan et al. .......................... 623/16 |
| 4,563,489 | 1/1986 | Urist ....................................... 623/16 |
| 4,578,384 | 3/1986 | Hollinger ................................. 519/8 |
| 4,596,574 | 6/1986 | Urist ....................................... 623/16 |
| 4,608,199 | 8/1986 | Caplan et al. . |
| 4,609,551 | 9/1986 | Caplan et al. . |
| 4,620,327 | 11/1986 | Caplan et al. . |
| 4,636,526 | 1/1987 | Dorman et al. . |
| 4,642,120 | 2/1987 | Nevo et al. . |
| 4,713,076 | 12/1987 | Draenert ................................. 623/16 |
| 4,749,585 | 6/1988 | Greco et al. ............................. 427/2 |
| 4,752,294 | 6/1988 | Lundgren . |
| 4,846,835 | 7/1989 | Grande ................................... 623/11 |
| 4,938,763 | 7/1990 | Dunn et al. . |
| 4,962,091 | 10/1990 | Eppstein et al. ........................ 514/2 |
| 4,964,868 | 10/1990 | Bloebaum ............................... 623/20 |
| 5,041,138 | 8/1991 | Vacanti et al. . |
| 5,061,281 | 10/1991 | Mares et al. ............................ 623/11 |
| 5,077,049 | 12/1991 | Dunn et al. . |
| 5,078,744 | 1/1992 | Chvapil ................................... 623/16 |
| 5,133,755 | 7/1992 | Brekke . |
| 5,152,791 | 10/1992 | Hakamatsuka et al. . |
| 5,288,496 | 2/1994 | Lewis ...................................... 424/426 |
| 5,294,446 | 3/1994 | Schlameus et al. . |
| 5,324,519 | 6/1994 | Dunn et al. ............................. 424/426 |
| 5,326,357 | 7/1994 | Kandel . |
| 5,366,508 | 11/1994 | Brekke . |
| 5,372,821 | 12/1994 | Badylak et al. ......................... 623/11 |
| 5,376,118 | 12/1994 | Kaplan et al. .......................... 623/11 |
| 5,425,639 | 6/1995 | Anders ................................... 433/169 |
| 5,478,739 | 12/1995 | Slivka et al. ............................ 623/13 |
| 5,512,475 | 4/1996 | Naughton et al. ...................... 623/11 |
| 5,520,923 | 5/1996 | Tjia et al. . |
| 5,569,463 | 10/1996 | Hezmus et al. ......................... 424/426 |
| 5,607,474 | 3/1997 | Athanasiou et al. .................... 623/16 |
| 5,616,338 | 4/1997 | Fox, Jr. et al. .......................... 424/423 |
| 5,645,084 | 7/1997 | McKay . |
| 5,665,114 | 9/1997 | Wendock . |
| 5,830,493 | 11/1998 | Yokota et al. . |

FOREIGN PATENT DOCUMENTS

| | | |
|---|---|---|
| 1274179 | 9/1990 | Canada . |
| 0277678 | 10/1988 | European Pat. Off. . |
| 0369034 | 5/1990 | European Pat. Off. . |
| 0505634 | 9/1992 | European Pat. Off. . |
| 0567391 | 4/1993 | European Pat. Off. . |
| 3841397 | 12/1988 | Germany . |
| 2164024 | 5/1985 | United Kingdom . |
| 2175506 | 12/1986 | United Kingdom . |
| WO8600533 | 1/1986 | WIPO . |
| WO8803785 | 6/1988 | WIPO . |
| WO9009783 | 9/1990 | WIPO . |
| WO9015586 | 12/1990 | WIPO . |
| WO9315694 | 8/1993 | WIPO . |
| WO9320859 | 10/1993 | WIPO . |

WO9409722 5/1994 WIPO.

OTHER PUBLICATIONS

Controlled Release of TGF–B, From a Biodegradable Matrix for Bone Regeneration, J.Biomater, Sci. Polymer Edn., vol. 5 No. 1/2, pp. 49–63, 1993.

Culture and differentiation of chondrocytes entrapped in alginate gels, by M. Grandolfo, P. D'Andrea, S. Paoletti, M. Martina, G. Silverstrini, E. Bonucci, and F. Vittur, Calcif. Tissue Int., 52, pp. 42–48, (1993).

Influence of matricial molecules on growth and differentiation of entrapped chondrocytes, by H. Ramdi, C. Legar, and M. Lievremont, Experi. Cell Res., 207, pp. 449–454, (1993).

Rabbit articular chondrocytes in alginate gel: characterisation of immobilized preparations and potential applications, by C. Tamponnet, H. Ramdi, J–B. Guyot, and M. Lievremont, Appl. Microbiol. Biotechnol., 37, pp. 311–315, (1992).

Synthesis and turnover of proteoglycans by human and bovine adult articular chondrocytes cultured in alginate beads, by H.J. Hauselmann, M.B. Aydelotte, B.L. Schumacher, K.E. Kuettner, S.H. Gitelis, and E.J.–M.A. Thonar, Matrix, 12, pp. 116–129, (1992).

Towards a synthetic articular cartilage, by P.H. Corkhill, J.H. Fitton, and B.J. Tighe, J. Biomater. Sci. Polymer Edn., 4 (6), pp. 615–630, (1993).

Neocartilage formation in vitro and in vivo using cells cultured on synthetic biodegradable polymers, by L.E. Freed, J.C. Marguis, A. Nohria, J. Emmanual, A.G. Mikos, and R. Langer, J. Biomed. Mat. Res., 27, pp. 11–23, (1993).

Porous polymer implants for repair of full–thickness defects of articular cartilage: an experimental study in rabbit and dog, by J. Klompmaker, H.W.B. Jansen, R.P.H. Veth, H.K.L. Nielson, J.H. de Groot, and A.J. Pennings, Biomat., 13 (9), pp. 625–634, (1992).

Laminated three–dimensional biodegradable foams for use in tissue engineering, by A.G. Mikos, G. Sarakinos, S.M. Leite, J.P. Vacanti, and R. Langer, Biomat., 14 (5), pp. 323–330, (1993).

Preparation of poly(glycolic acid) bonded fiber structures for cell attachment and transplantation, by A.G. Mikos, Y. Bao, L.G. Cima, D.E. Ingber, J.P. Vacanti, and R. Langer, J. Biomed. Mat. Res., 27, pp. 183–189, (1993).

Effect of freeze–dried poly–L–lactic acid discs mixed with bone morphogenetic protein on the healing of rat skull defects by T. Miki, K. Harada, Y. Imai, and S. Enomoto, J. Oral Maxillofac. Surg., 52, pp. 387–391, (1994).

Attachment and survival of perichondrocytes in a porous polylactic acid (PLA) matrix: an in vitro study, by C.R. Chu, A.Z. Monosov, R.D. Coutts, and D. Amiel, Thirteenth Southern Biomedical Engineering Conference, Apr. 16–17, 1994, University of the Districk of Columbia, Washington, D.C.

Identification of hyaluronic acid binding sites in the extracellular domain of CD44, by R.J. Peach, D. Hollenbaugh, I. Stamenkovic, and A. Aruffo, J. Cell Bio., 122 (1), pp. 257–264 (Jul. 1993).

Hyaluronate can function as a cell adhesion molecule and CD44 participates in hyaluronate recognition, by K. Miyake, C.B. Underhill, J. Lesley, and P.W. Kincade, J. Exp. Med., 172, pp. 69–75, (1990).

Expression and modulation of CD44 variant isoforms in humans, by C.R. Mackay, H–J. Terpe, R. Stauder, W.L. Marston, H. Stark and U. Günthert, J. Cell Bio., 124 (1&2), pp. 71–82, (Jan.1994).

Application of Porous Ceramics for the Attachment of Load Bearing Internal Orthopedic Applications, J.J. Klawitter et al., Bioceramics—Engineering in Medicine (Part 1), J. Biomedical Materials Symposium, No. 2, pp. 161–229 (1972).

Bioceramics—Engineering in Medicine (Part 2), J. Biomedical Materials Symposium, R. Topazian et al., No. 2 (Part 2), pp. 311–332 (1972).

The Repair of Experimentally Produced Defects in Rabbit Articular Cartilage by Autologous Chondrocyte Transplantation, D.A. Grande et al., Journal of Orthopaedic Research, vol. 7, No. 2, pp. 208–218, 1989.

The use of polylactic acid matrix and periosteal grafts for the reconstruction of rabbit knee articular defects, H.P. von Schroeder et al., Journal of Biomedical Materials Research, vol. 25, pp. 329–339 (1991).

New Insights on the Degradation of Bioresorbable Polymeric Devices Based on Lactic and Glycolic Acids, by Vert et al., Clinical Materials 10, 1992 pp. 3–8.

Structure and Function of Plasma Proteins, vol. 1, Plenum Press, London and New York, pp. 136–137.

Human Biochemistry, The C.V. Mosby Company, St. Louis, p. 440, 1982.

Polylactic Acid Surgical Dressing Materials Postoperative Therapy for Dental Extraction Wounds, J Canad. Dent. Assn. No. 7, 1986, pp. 599–602.

Calvaria Repair in Monkeys Using Alloplastic–Alloimplants, The 13th Annual Meeting of the Society for Biomaterials, Jun. 2–6, 1987, New York, New York.

An evaluation of two configurations of tricalcium phosphate for treating craniotomies, J. Biomedical Materials Research, vol. 23, No. 1, Jan. 1989, pp. 17–29.

Spence, "Basic Human Anatomy", 1986, pp. 63–65.

Cartilage resurfacing of the rabbit knee, E. Billings, Jr. et al., Acta Orthop Scand 1990; 61(3), pp. 201–206.

Potential of Adult Human Perichondrium to Form Hyalin Cartilage In Vitro, S.K. Bulstra et al., Journal of Orthopaedic Research, vol. 8, No. 3, 1990, pp. 328–335.

The use of demineralized bone and rib perichondrium composite grafts for the repair of full thickness articular defects, H.P. von Schroeder et al., 36th Annual Mtg, Orthopaedic Research Society, Feb. 5–8, 1990, New Orleans.

Reconstruction of rabbit knee articular defects with a polylactic acid matrix, R.D. Coutts et al., Orthopaedic Research Society, Feb. 5–8, 1990.

Culture–Expanded Human Periosteal–Derived Cells Exhibit Osteochondral Potential In Vivo, H. Nakahara et al., and Journal of Orthopaedic Research, vol. 9, No. 4, 1991, pp. 465–476.

Polymers, R. Langer, Bone Symposium '91, Oregon Health Sciences University, Portland, Oregon, Jul. 17–20, 1991, pp. 367–373.

The Repair of Full–Thickness Articular Cartilage Defects, N. Kawabe et al., Clinical Orthopaedics and Related Research, No. 268, Jul., 1991, pp. 279–293.

Reconstruction of rabbit knee articular defects with a polylactic acid matrix and periosteal grafts, R.D. Coutts et al., Combined Meeting/Orthopaedic Research Societies, Oct. 21–23, 1991.

Growth factor responsiveness of perichondrial cells in monolayer and attached to polylactic acid carriers, M. Lotz et al., American College of Rheumatology, Nov. 17–21, 1991.

Rib Periocondrial Autografts in Full–Thickness Articular Cartilage Defects in Rabbits, R.D. Coutts et al., Clinical Orthopaedics, Feb. 1992, vol. 275, pp. 263–273.

The Effect of a TCP–Collagen Implant on the Healing of Articular Cartilage Defects in the Rabbit Knee Joint, T. Hogervorst et al., Journal of Applied Biomaterials, vol. 3, pp. 251–258, (1992).

Bioresorbability and Biocompatibility of Aliphatic Polyesters, M. Vert et al., Journal of Materials Science: Materials in Medicine 3, ©1992 Chapman & Hall, pp. 432–446.

In vivo degradation of massive poly(a–hydroxy acids): validation of in vitro findings, by M. Therin et al., Biomaterials vol. 13, No. 9, ©1992 pp. 594–600.

Scientific American, Aug. 1992, Science and Business, pp. 114–116, Materials Help, Bioengineers produce versions of body tissues, by Deborah Erickson.

Guidor, The Bioresorbable Matrix Barrier, pp. 1–33 (1993).

Compressive Characteristics of Freeze–Dried Agar and Alginate Gel, A. Nussinovitch et al., Biotechnol Prog, pp. 101–104 (1993).

Mechanisms of polymer degradation in implantable devices. 2. Poly(DL–lactic acid), S.A.M. Ali et al., Journal of Biomedical Materials Research, vol. 27, ©1993 pp. 1409–1418.

Evidence for the existence of hyaluronectin–binding proteins in the plasma membranes, Sanjay Gupta et al., FEBS 13470, vol. 336, pp. 511–515 (1993).

Resorbable Ceramic Implants, G.A. Graves et al., Bioceramics—Engineering in Medicine (Part 1), J. Biomedical Materials Symposium, No. 2, pp. 91–115 (1972).

Compatibility of Porous Ceramics with Soft Tissue; Application to Tracheal Prosthesis, S.F. Hulbert et al., Bioceramics—Engineering in Medicine (Part 1), J. Biomedical Materials Symposium, vol. 2, (Part 1), pp. 269–279 (1972).

Development of Ceramic and Ceramic Composite Devices for Maxillofacial Applications, T.D. Driskell et al., Bioceramics—Engineering in Medicine (Part 2), J. Biomedical Materials Symposium, No. 2 (Part 2), pp. 345–361 (1972).

Effect of Surgical Trauma and Polylactate Cubes and Granules on the Incidence of Alveolar Osteitis in Madibular Third Molar Extraction Wounds, John Brekke et al., J. Canad Dent Assn, No. 4 pp. 315–319 (1986).

Repair of Articular Surfaces by Allografts of Articular and Growth–Plate Cartilage, by J.E. Aston et al., The Journal of Bone and Joint Surgery, vol. 68–B, No. 1, Jan. 1986.

Sato et al., Pharm. Res., 5 (1), 21–30, 1988, Porous biodegradable microspheres for controlled drug delivery.

The Effect of the Addition of Low Molecule Weight Poly-(DL–lactide) on Drug Release from Biodegradable Poly-(DL–lactide) Drug delivery Systems, R. Bodmeier et al., International Journal of Pharmaceutics, 51, pp. 1–9, (1989).

Repair of Rabbit Articular Surfaces with Allograft Chondrocytes Embedded in Collagen Gel, by S. Wakitani et al., The Journal of Bone and Joint Surgery, vol. 71–B, No. 1, Jan. 1989, pp. 74–80.

The use of polylactic acid matrix and periosteal grafts for the reconstruction of rabbit knee articular defects, H.P. von Schroeder et al., Society For Biomaterials, May 20–23, 1990.

In Vivo Osteochondrogenic Potential of Cultured Cells Derived From the Periosteum, H. Nakahara et al., Clinical Orthopaedics, Oct. 1990, vol. 259, pp. 223–232.

Effect of the Structure of Poly(Glycol Monomethacrylate) Gel on the Calcification of Implants, L. Sprinel et al., Calc. Tiss., Res. 13 pp. 63–72 (1973).

Calcium Phosphate Ceramics as Hard Tissue Prosthetics, Michael Jarcho, PH.D., Clinical Orthopaedics and Related Research, No. 157, pp. 259–278 (1981).

Developmental Role of Hyaluronate, Bryan P. Toole, Connective Tissue Research, vol. 10, pp. 93–100 (1982).

Effect of fibronectin on the adhesion of an established cell line to a surface reactive biomaterial, T.L. Seitz et al., Journal of Biomedical Materials Research, vol. 16, pp. 195–207 (1982).

Influence of polylactic acid mesh on the incidence of localized osteitis, John H. Brekke et al., Oral Surg., vol. 56, No. 3, pp. 240–245 (1983).

Healing of Hyaluronic Acid–Enriched Wounds: Histological Observations, G. Abatangelo et al., Journal of Surgical Research 35, pp. 410–416 (1983).

Human Bone Morphongenetic Protein, Marshall R. Urist et al., Proceedings of the Society for Experimental Biology and Medicine 173, pp. 194–199 (1983).

Urist et al., Proc. Natl. Acad. Sci. USA, vol. 81, Jan. 1984 pp. 371–375, Purification of Bovine Bone Morphogenetic Protein by Hydroxyapatite Chromatograph.

Beta–tricalcium Phosphate Delivery System for Bone Morphogenetic Protein, Marshall R. Urist et al., Clinical Orthopaedics and Related Research, No. 187, pp. 277–280 (1984).

*Primary Examiner*—Robert A. Clarke
*Attorney, Agent, or Firm*—Alan Kamrath; Peterson, Wicks, Nemer & Kamrath, P.A.

[57] ABSTRACT

An anatomically specific, bioresorbable, implant device for facilitating the healing of voids in bone, cartilage and soft tissue is disclosed. A preferred embodiment of using the implant device for facilitating the healing of a human joint lesion includes a cartilage region invested with an alginate microstructure joined with a subchondral bone region invested with a hyaluronan microstructure. The alginate selectively dispersed in the cartilage region enhances the environment for chondrocytes to grow articular cartilage. The hyaluronan selectively dispersed in the subchondral bone region enhances the environment for mesenchymal cells which migrate into that region's macrostructure and which differentiate into osteoblasts. The microstructures can be invested at varying concentrations in the regions. A hydrophobic barrier, strategically positioned within the subchondral bone region macrostructure, shields the chondrocytes from the oxygenated blood in subchondral cancellous bone. In the preferred form, the cartilage region includes a tangential zone including a network of intercommunicating void spaces having a horizontal orientation and in communication with synovial fluid and includes a radial zone including multiple void spaces oriented in both horizontal and vertical planes and providing intercommunication between the tangential zone and the subchondral bone region.

42 Claims, 5 Drawing Sheets

DEVICE AND METHODS FOR IN VIVO CULTURING OF DIVERSE TISSUE CELLS

BACKGROUND

The present invention generally relates to the transport and culturing of cells.

The medical repair of bones and joints in the human body presents significant difficulties, in part due to the materials involved. Each bone has a hard, compact exterior surrounding a spongy, less dense interior. The long bones of the arms and legs, the thigh bone or femur, have an interior containing bone marrow. The material that bones are mainly composed of is calcium, phosphorus, and the connective tissue substance known as collagen.

Bones meet at joints of several different types. Movement of joints is enhanced by the smooth hyaline cartilage that covers the bone ends and by the synovial membrane that lines and lubricates the joint. For example, consider a cross-section through a hip joint. The head of the femur is covered by hyaline cartilage. Adjacent to that cartilage is the articular cavity. Above the articular cavity is the hyaline cartilage of the acetabulum which is attached to the ilium. The ilium is the expansive superior portion of the hip bone.

Cartilage damage produced by disease such as arthritis or trauma is a major cause of physical deformity and dehabilitation. In medicine today, the primary therapy for loss of cartilage is replacement with a prosthetic material, such as silicon for cosmetic repairs, or metal alloys for joint realignment. The use of a prosthesis is commonly associated with the significant loss of underlying tissue and bone without recovery of the full function allowed by the original cartilage. The prosthesis is also a foreign body which may become an irritating presence in the tissues. Other long-term problems associated with the permanent foreign body can include infection, erosion and instability.

The lack of a truly compatible, functional prosthesis subjects individuals who have lost noses or ears due to burns or trauma to additional surgery involving carving a piece of cartilage out of a piece of lower rib to approximate the necessary contours and insert the cartilage piece into a pocket of skin in the area where the nose or ear is missing.

In the past, bone has been replaced using actual segments of sterilized bone or bone powder or porous surgical steel seeded with bone cells which were then implanted. In most cases, repair to injuries was made surgically. Patients suffering from degeneration of cartilage had only pain killers and anti-inflammatories for relief.

Until recently, the growth of new cartilage from either transplantation or autologous or allogeneic cartilage has been largely unsuccessful. Consider the example of a lesion extending through the cartilage into the bone within the hip joint. Picture the lesion in the shape of a triangle with its base running parallel to the articular cavity, extending entirely through the hyaline cartilage of the head of the femur, and ending at the apex of the lesion, a full inch (2.54 cm) into the head of the femur bone. Presently, there is a need to successfully insert an implant device consisting of a macrostructure and a microstructure for containing and transporting cartilage cells and bone cells together with supporting nutrients, growth factors and morphogens, which will assure survival and proper future differentiation of these cells after transplantation into the recipient tissue defect. Presently, cartilage cells, called chondrocytes, when implanted along with bone cells, can degenerate into more bone cells because hyaline cartilage is an avascular tissue and must be protected from intimate contact with sources of high oxygen tension such as blood. Bone cells, in contrast, require high oxygen levels and blood.

Most recently, two different approaches to treating articular lesions have been advanced. One approach such as disclosed in U.S. Pat. No. 5,041,138 is coating bioderesorbable polymer fibers of a structure with chemotactic ground substances. No detached microstructure is used. The other approach such as disclosed in U.S. Pat. No. 5,133,755 uses chemotactic ground substances as a microstructure located in voids of a macrostructure and carried by and separate from the biodegradable polymer forming the macrostructure. Thus, the final spatial relationship of these chemotactic ground substances with respect to the bioresorbable polymeric structure is very different in U.S. Pat. No. 5,041,138 from that taught in U.S. Pat. No. 5,133,755.

The fundamental distinction between these two approaches presents three different design and engineering consequences. First, the relationship of the chemotactic ground substance with the bioresorbable polymeric structure differs between the two approaches. Second, the location of biologic modifiers carried by the device with respect to the device's constituent materials differs. Third, the initial location of the parenchymal cells differs.

Both approaches employ a bioresorbable polymeric structure and use chemotactic ground substances. However, three differences between the two approaches are as follows.

I. Relationship of Chemotactic Ground Substances with the Bioresorbable Polymeric Structure The design and engineering consequence of coating the polymer fibers with a chemotactic ground substance is that both materials become fused together to form a single unit from structural and spatial points of view. The spaces between the fibers of the polymer structure remain devoid of any material until after the cell culture substances are added.

In contrast, the microstructure approach uses chemotactic ground substances as well as other materials, separate and distinct from the bioresorbable polymeric macrostructure. The microstructure resides within the void spaces of the macrostructure and only occasionally juxtaposes the macrostructure. Additionally, the microstructure approach uses polysaccharides and chemotactic ground substances spacially separate from the macrostructure polymer and forms an identifiable microstructure, separate and distinct from the macrostructure polymer.

The design and engineering advantage to having a separate and distinct microstructure capable of carrying other biological active agents can be appreciated in the medical treatment of articular cartilage. RGD attachment moiety of fibronectin is a desirable substance for attaching chondrocytes cells to the lesion. However, RGD attachment moiety of fibronectin is not, by itself, capable of forming a microstructure of velour in the microstructure approach. Instead, RGD is blended with a microstructure material prior to investment within macrostructure interstices and is ultimately carried by the microstructure velour.

II. Location of Biologic Modifiers Carried by a Device with Respect to the Device's Constituent Materials Coating only the polymer structure with chemotactic ground substances necessarily means that the location of the chemotactic ground substance is only found on the bioresorbable polymeric structure fibers. The microstructure approach uses the microstructure to carry biologic modifiers such as growth factors, morphogens, drugs, etc. The coating approach can only carry biologic modifiers with the biodegradable polymeric structure.

III. Initial Location of the Parenchymal Cell

Because the coating approach attaches the chemotactic ground substances to the surfaces of the structure polymer and has no microstructure resident in the void volume of the device, the coating approach precludes the possibility of establishing a network of extracellular matrix material, specifically a microstructure, within the spaces between the fibers of the polymer structure once the device is fully saturated with cell culture medium. The coating approach predetermines that any cells introduced via culture medium will be immediately attracted to the surface of the structure polymer and attach thereto by virtue of the chemotactic ground substances on the polymer's surfaces.

The consequence of confining chemotactic ground substances to only the surfaces of the polymeric structure places severe restrictions on the number of cells that can be accommodated by the coated device. These restrictions on cell capacity are enforced by two limiting factors:

1) a severely limited quantity of chemotactic ground substance that can be incorporated within the device; and
2) a surface area available for cell attachment that is limited by the surface area supplied by the structure polymer.

In contrast to the coating approach, the microstructure approach, by locating chemotactic ground substances in the void spaces of the device, makes available the entire void volume of the device to accommodate their chemotactic ground substance microstructure.

SUMMARY OF THE INVENTION

The anatomically specific device is a living prosthesis or implant for transport and for in vivo culturing of tissue cells in a diverse tissue lesion. The entire macrostructure of this device is composed of a bioresorbable polymer.

The anatomically specific device integrates a macrostructure, microstructure, free precursor cells cultured in vitro or from tissue, and biologically active agents, such as associated growth factors, morphogens, drugs and therapeutic agents.

The anatomically specific device in the embodiment designed for treating a cartilage and bone lesion has two main regions: a cartilage region and a subchondral bone region.

The cartilage region has a macrostructure composed of two distinct zones. The tangential zone of the cartilage region has intimate contact with synovial fluid. The radial zone located between the tangential zone and the subchondral bone region and comprising about 70% to 90% of the cartilage region is distinguished by vertically oriented plates which are fenestrated by multiple voids. The radial zone of the cartilage region is intimately bound to the macrostructure of the subchondral region at an interface surface.

The microstructure material of the cartilage region in the most preferred form is alginate or hyaluronan. Alginate, also known as alginic acid, is used for the transport of both in vitro and in vivo cultured cells and the establishment of an in vivo cell culture system within the device. Alginic acid, though having no chemotactic properties, is especially suitable for use in a device for treating articular cartilage defects because it facilitates the culturing and transport of chondrocytes.

The structure and the strategic location of the alginate microstructure inside the macrostructure provides the opportunity to segregate microstructure material from the subchondral bone region. The alginate microstructure has a primary function of delivering chondrocytes only to the cartilage region of the device by sequestering the chondrocyte cell population with the in vitro cell culture medium in its alginate gel. The microstructure has a secondary function of presenting enough chondrocytes to the subchondral bone region immediately adjacent to the cartilage regions to establish a competent osteo-chondral bond.

The selective concentration gradient of microstructure material may be selectively varied within certain regions of the macrostructure void to affect different biologic characteristics critical to different tissue requirements.

The microstructure of a single device may be composed of multiple different materials, some without chemotactic properties, in different regions of macrostructure void space depending upon varying tissue and biologic characteristics and requirements.

The subchondral bone region of the anatomically specific device includes a macrostructure composed of a biologically acceptable, bioresorbable polymer arranged as a one piece porous body with "enclosed randomly sized, randomly positioned and randomly shaped interconnecting voids, each void communicating with all the others, and communicating with substantially the entire exterior of the body" (quoted portion from U.S. Pat. No. 4,186,448). Polylactic acid (PLA), fabricated in the 3-D architecture of intercommunicating voids described above is the polymer currently used to form the macrostructure. Other members of the hydroxy acid group of compounds can also be used as can any bioresorbable polymer if fabricated into a similar architecture.

The gross, or macro, structure of the invention fulfills three major functions for chondrogenesis and osteogenesis: 1) restoration of mechanical architectural and structural competence; 2) provides biologically acceptable and mechanically stable surface structure suitable for genesis, growth and development of new non-calcified and calcified tissue; and 3) functions as a carrier for other constituents of the invention which do not have mechanical and structural competence.

The microstructure of the implant device is composed of various polysaccharides which, in a preferred form, is alginate but can also be hyaluronic acid (abbreviated by HY). Interstices of the polylactic acid macrostructure of the body member are invested with the microstructure substance in the form of a velour having the same architecture of interconnecting voids as described for the macrostructure, but on a microscopic scale. Functions of the chemotactic ground substance microstructure (i.e. HY) are listed as: 1) attraction of fluid blood throughout the device; 2) chemotaxis for mesenchymal cell migration and aggregation; 3) carrier for osteoinductive and chondro-inductive agent(s); 4) generation and maintenance of an electro-negative wound environment; and 5) agglutination of other connective tissue substances with each other and with itself. Other examples of chemotactic ground substances are fibronectin and, especially for the reconstruction of articular cartilage, an RGD attachment moiety of fibronectin.

The osteoinductive agent, bone morphogenetic protein, has the capacity to induce primitive mesenchymal cells to differentiate into bone forming cells. Another osteogenic agent, bone derived growth factor, stimulates activity of more mature mesenchymal cells to form new bone tissue. Other biologically active agents which can be utilized, especially for the reconstruction of articular cartilage, include transforming growth factor β (beta) and basic fibroblastic growth factor.

In a further aspect of the present invention, the anatomically specific implant device acts as a transport device of precursor cells harvested for the production of connective tissue. The device with its secured precursor cells can be press fit into the site of lesion repair. In a preferred aspect of the present invention, the microstructure velour (i.e. hyaluronan or alginate in the most preferred form) treated with an RGD attachment moiety of fibronectin facilitates the attachment of free, precursor cells to be carried to the lesion repair site.

Significant advantages and features of the present invention include:

1. The arrangement of fenestrated polymer strands of the tangential region produces a network of intercommunicating void spaces which have a horizontal orientation with respect to void spaces of the radial zone, thus making this construction anatomically specific for articular cartilage tissue.
2. The cartilage region's radial zone provides void spaces in horizontal planes which penetrate the vertically orientated polymer sheets and create intercommunications between the vertically positioned void spaces.
3. The radial zone of the cartilage region at the interface surface with the subchondral bone region provides a honeycomb pattern of pores with an uninterrupted space communicating from the interface surface, through the radial and tangential zones, to the pores which ultimately accesses the synovial fluid.
4. The hydrophobic barrier creates a strategic zone without interrupting the continuity of the macrostructure polymer of the subchondral bone region and further without introducing any chemical change in the macrostructure polymer.
5. The microstructure is strategically located within one, or multiple, discrete locales of the macrostructure void network while other locales of the macrostructure void network remain devoid of microstructure material.
6. The concentration gradients of microstructure material are selectively varied within certain regions of macrostructure voids to affect different biologic characteristics critical to different tissue requirements.
7. A microstructure is provided to a single anatomically specific device having a composition of multiple different materials in different regions of macrostructure voids according to the varying tissue and biologic characteristic requirements.
8. The use of a microstructure within a macrostructure provides multiple locations for transport of one or more types of biologic modifier cargo:
   1) onto the surface of the macrostructure;
   2) entrapped between the macrostructure and the microstructure;
   3) onto the surface of the microstructure;
   4) inside the microstructure; and/or
   5) within the hydration domains of the microstructure and yet detached from the polysaccharide of the microstructure as well as detached from the polymer of the macrostructure.
9. The three-dimensional configuration of the cell is preserved.
10. The entire surface area of each cell is preserved in optimum condition for interaction with the microstructure and its cargo of biologically active agents.
11. Each cell is coated with microstructure material which, in the case of hyaluronic acid, is composed of a high percentage of naturally occurring extracellular matrix.
12. Free cells are maintained in a semi-fluid environment so that the cells can move to establish multiple regions of optimum cell density.
13. The cells are maintained in close proximity to high concentrations of free, solubilized and unattached biologically active agents.
14. A transport for biologically active agents is provided.
15. A transport for osteoinductive/osteogenic and/or chondroinductive/chondrogenic agents, as well as other therapeutic substances (i.e. living cells appropriate for the tissue under treatment, cell nutrient media, varieties of growth factors, morphogens and other biologically active proteins) are provided.
16. An electronegative environment is created which is conducive to osteogenesis/chondrogenesis.
17. The need for more surgery to remove the device is eliminated since it is bioresorbable in its entirety.
18. A transport for precursor repair cells to lesion repair sites is created.
19. The attachment of free, precursor cells to the device and to the repair site is facilitated.

Objects of the present invention include:

1. Joins bioresorbable polymers of different architectures and chemical profiles into a single unit whose composite architectures are specifically ordered to duplicate the arrangements of parenchymal cells and stromal tissue of the tissue or organ under treatment and whose constituent polymers are specifically synthesized to possess chemical profiles appropriate for their particular locations within the whole. This object of the invention is expressed in the example of a device for treatment of articular cartilage defects in the most preferred form. The cartilage region architecture is joined to the subchondral bone region (cancellous bone) architecture to form a bioresorbable polymer implant having an anatomically specific architecture for articular cartilage.
2. Strategically positions microstructure material in that specific portion of the complete device to perform the particular unique functions required by the particular tissues being treated.
3. Segregates microstructure material within the anatomically specific device according to the special biologic functions of a particular implant.
4. Delivers chondrocytes only to the cartilage region of the device and supports their life functions in the cartilage defect by sequestering the chondrocyte cell population together with the in vitro cell culture medium in its microstructure (alginate) gel.
5. Presents enough chondrocytes to the subchondral bone region immediately adjacent to the cartilage region so as to assure that a competent osteo-chondral bond is established between the newly developed cartilage and the newly developed bone.
6. Provides a bioresorbable structure to carry and to support cell attachment enhancing material such as a chemotactic ground substance which is in the form of a filamentous velour having incomplete, interconnecting intersticies.
7. Generates electronegative potentials by maintaining an alginate or HY-fluid phase and PLA structural phase interface, as well as by the electronegative chemical property of alginate or HY alone.
8. Creates biophysical conditions and environment such that exogenous electric signals can be applied to the implant device to produce a synergistic effect with the endogenous currents generated by alginate or HY/PLA surface interactions and the intrinsic electronegativity of the microstructure.

9. Provides a unique juxtaposition of polylactate, alginate/ hyaluronic acid and chemical osteoinductive/ osteogenic and/or chondroinductive/chondrogenic agents.

10. Juxtaposes cell attachment enhancing material such as a chemotactic ground substance with a biodegradable polymer of either solid, open cell meshwork form, or in either form or both forms.

11. Provides a biodegradable structure to transport and to support precursor repair cells for repair sites.

12. Creates conditions and environments for facilitating the attachment of free, precursor cells for carriage to the repair site.

DESCRIPTION OF THE PREFERRED EMBODIMENTS

A device and method according to the preferred teachings of the present invention is disclosed for treating mammalian bone and cartilage deficiencies, defects, voids and conformational discontinuities produced by congenital disformities, osseous and/or soft tissue pathology, tramatic injuries, accidental and/or surgical, and functional atrophy. The primary purpose of the anatomically specific implant device of the preferred form of the present invention is to provide the means by which chondrocytes and their attendant synthesis products, principally collagen type II, cultured in vitro, can be transported into an articular cartilage defect and be safely established therein.

Specifically, the anatomically specific device according to the preferred teachings of the present invention consists of two main parts, the cartilage region and the subchondral bone region joined at an interface surface. Each of the cartilage and the subchondral bone regions of the device includes a macrostructure composed of a bioresorbable polymer either as homogeneous polymers or combinations of two or more co-polymers from groups of, for example, poly (alpha-hydroxy acids), such as polylactic acid or polyglycolic acid or their co-polymers, polyanhydrides, polydepsipeptides, or polyorthoester. Devices fabricated for prototypes of animal studies to-date have been fabricated from the homopolymer D,D-L,L-polylactic acid.

The bioresorbable polymer in the subchondral bone region in the most preferred form is in the architecture of cancellous bone such as of the type described in U.S. Pat. Nos. 4,186,448 and 5,133,755 which are hereby incorporated herein by reference.

Figure 1:
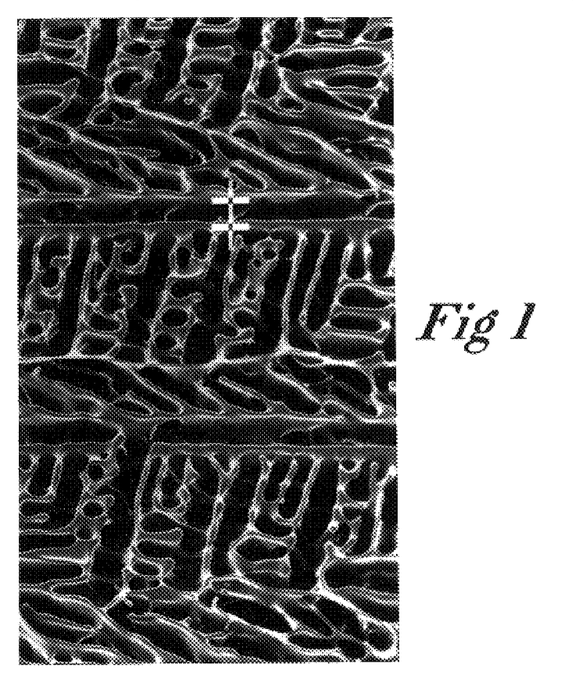
FIG. 1 is a top view of the macrostructure and architecture of the tangential zone of the cartilage region with no microstructure alginate shown.
Figure 2:
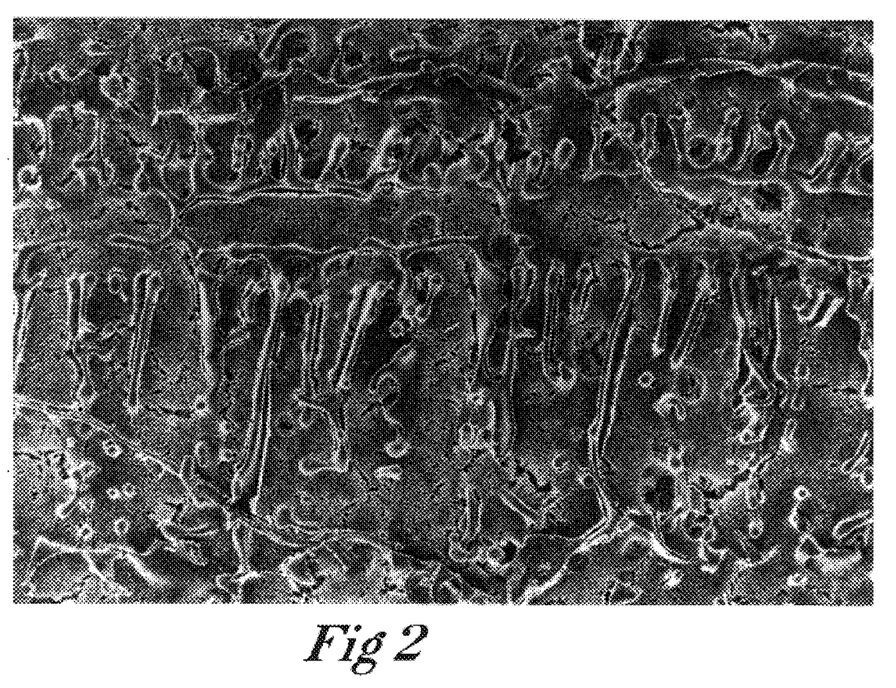
FIG. 2 is a top view of a cartilage region of a tangential zone as in FIG. 1 invested with alginate microstructure.
Figure 3:
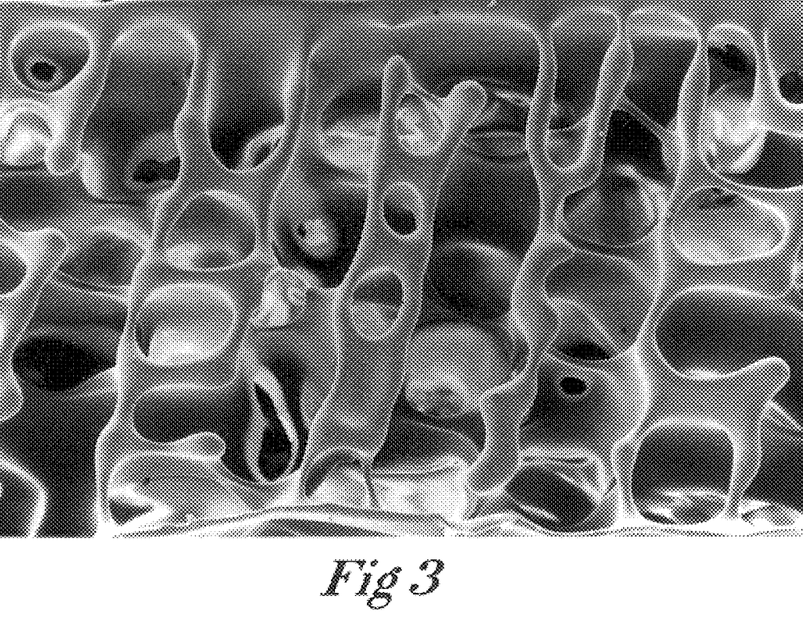
FIG. 3 is an enlarged view of FIG. 1.
Figure 4:
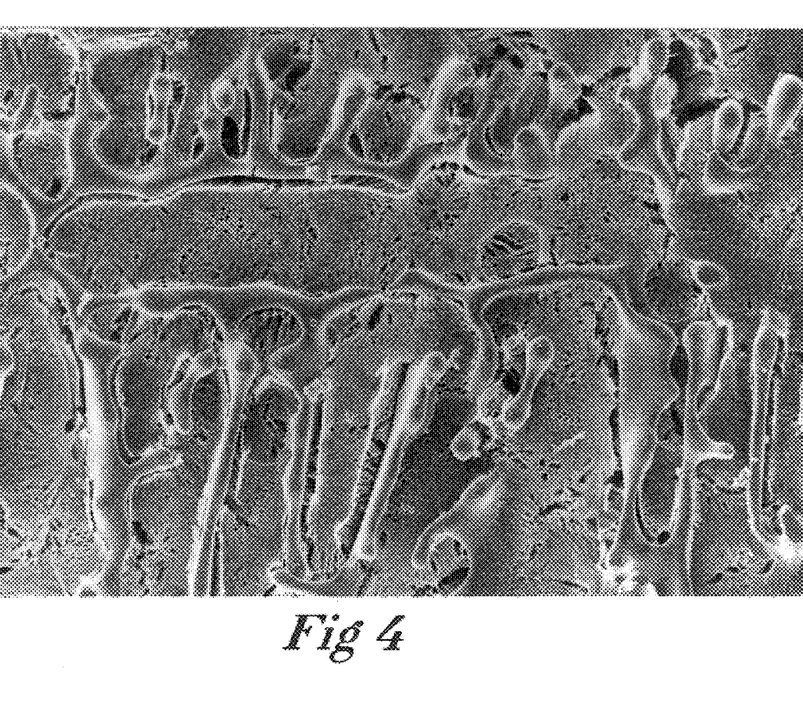
FIG. 4 is an enlarged view of FIG. 2.
Figure 5:
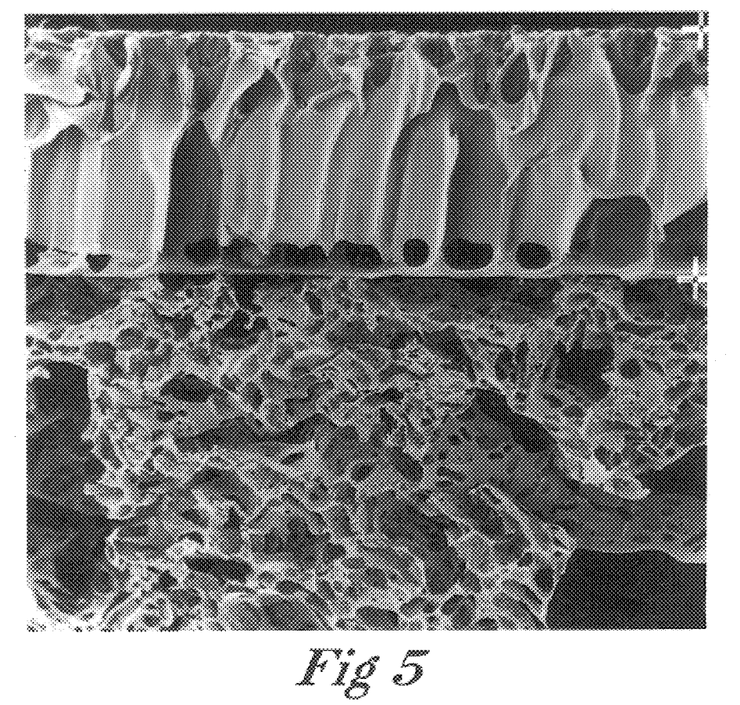
FIG. 5 is a cross-sectional view through the entire device without any microstructure.

The cartilage region comprises 10% to 30% of the anatomically specific device and contains a tangential zone and a radial zone each having an architecturally distinct pattern. The radial zone is located intermediate or between the tangential zone and the subchondral bone region. The tangential zone is approximately 100 micrometers thick in a vertical direction and has intimate contact with the synovial fluid. Hereinafter, vertical refers to an orientation situated at right angles to the interface of the cartilage tissue with subchondral bone or in other words an orientation at right angles to the interface surface between the cartilage and subchondral bone regions of the device. This tangential zone is formed by major polymer strands which run parallel to each other and are arranged in a horizontal plane forming horizontal channels approximately 100 to 120 micrometers wide in a horizontal direction. Hereinafter, horizontal refers to an orientation situated parallel to the interface of cartilage tissue with subchondral bone or in other words an orientation parallel to the interface surface between the cartilage and subchondral bone regions of the device. The channels formed by the major polymer strands are separated from each other by a network of minor polymer strands. These minor polymer strands are also arranged in a horizontal plane, join the major polymer strands at approximately right angles, and are approximately 650 micrometers in length in a horizontal direction. All polymer strands of the tangential zone are fenestrated by multiple void spaces. The arrangement of fenestrated polymer strands produces a network of intercommunicating void spaces which have a horizontal orientation with respect to the void spaces of the radial zone.

The radial zone comprises 70% to 90% of the cartilage region. The radial zone is composed of vertically arranged, thin sheets of polymer which are fenestrated by multiple void spaces oriented in both horizontal and vertical planes. The vertically oriented void spaces of the radial zone extend, uninterrupted, from the interface surface of the cartilage and subchondral bone regions to the tangential zone. Void spaces in the horizontal plane penetrate the vertically oriented polymer sheets and create intercommunications between the vertically positioned void spaces.

Figure 8:
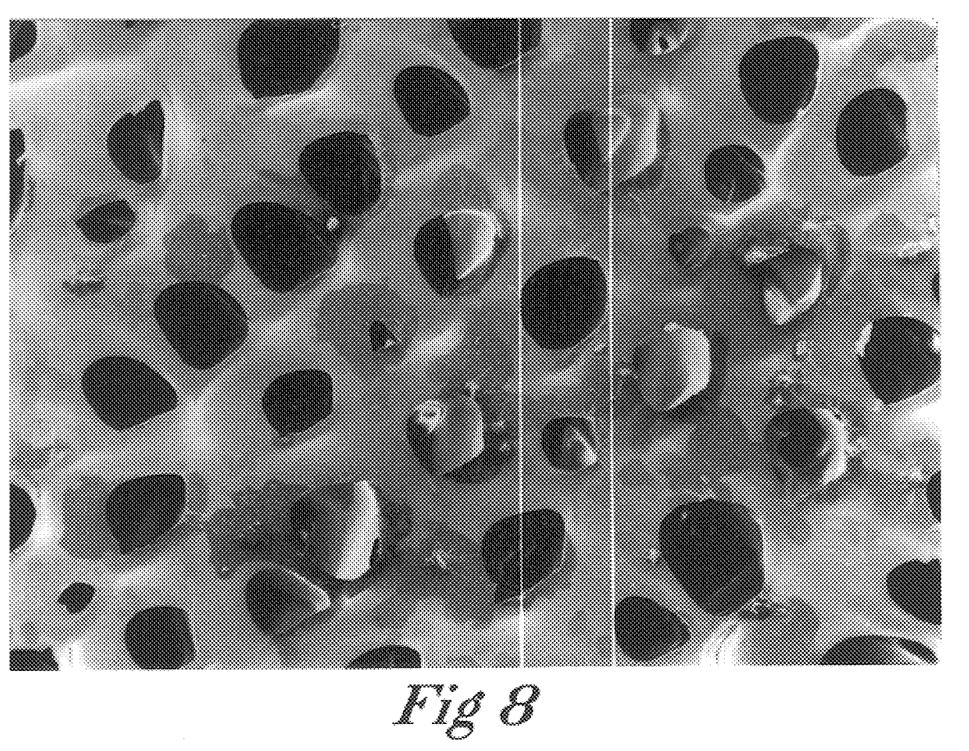
FIG. 8 is a cross-sectional view of the radial zone of the cartilage region at the interface surface.
Figure 9:
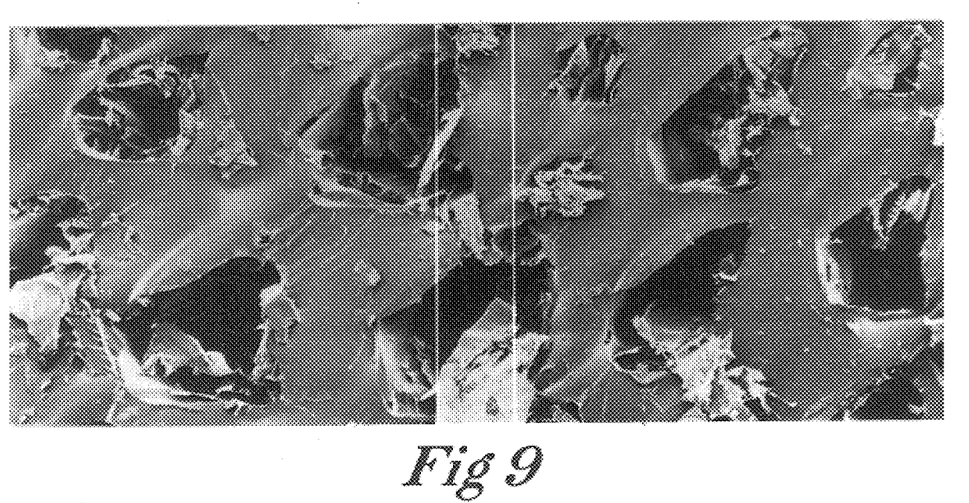
FIG. 9 is a cross-sectional view of the radial zone of cartilage region at the interface surface with alginate invested into the interstices.

The radial zone at the interface surface reveals the vertically oriented void spaces of the radial zone in cross section. The pattern of the radial zone at the interface surface formed may be described as a honeycomb pattern composed of discrete pores. The majority of discrete pores measure approximately 200 to 250 micrometers in feret diameter. These pores are generally circular. Some pores are partially occluded by a thin polymer membrane. Through these pores, there is uninterrupted void space communication from the interface surface through the radial and tangential zones to the void spaces of the tangential zone which access synovial fluid.

The architecture of the cartilage region may be formed utilizing established techniques widely practiced by those skilled in the art of bioresorbable polymers. These methods include injection molding, vacuum foaming, spinning hollow filaments, solvent evaporation, soluble particulate leaching or combinations thereof. For some methods, plasticizers may be required to reduce the glass transition temperature to low enough levels so that polymer flow will occur without decomposition.

For the devices which were fabricated for use in a rabbit's knee, the cartilage region was limited to a thickness of about 1,000 micrometers plus or minus 200 micrometers. In a human, the cartilage region can be increased to a maximum of about 3.0 mm in thickness, specifically 3,000 micrometers.

The macrostructure polymer of the cartilage region is joined or bound to the macrostructure polymer of the subchondral bone region by a process such as heat fusion which does not involve the use of solvents or chemical reactions between the two polymer segments. The resulting union between the two architectural regions is very strong and can withstand any handling required to package the device as well as any forces delivered to it as a result of the implantation technique without distorting the device's internal architecture of void spaces.

Alginate is the microstructure material most preferred in the cartilage region for the transport of in vitro and in vivo cultured cells and for the establishment of an in vivo cell culture system within a bioresorbable implant. Alginate is especially suitable for use in an anatomically specific device for treating articular cartilage defects because alginate has no known angiogenic properties and has been used successfully by others to culture and transport chondrocytes.

Alginate is a polysaccharide derived from Phaeophyceae also known as brown seawood. The most common source of alginate is the species Macrocystis pyrifera, the giant kelp, which grows along the coasts of North and South America, New Zealand, Australia and Africa. Other polysaccharides, such as agar and carrageenan, extracted from various types of red algae, as well as hyaluronan, also make suitable microstructure materials for bioresorbable systems designed to transport and culture chondrocytes.

Alginate is a polysaccharide polymer composed of repeating units of D-mannuronic acid, repeating units of L-guluronic acid or alternating D-mannuronic acid and L-guluronic acid residues. The exact composition of a given alginate sample depends on the subspecies of kelp (*Macrocystis pyrifera*) from which it was derived.

The most preferred form of the present invention employs a refined sodium alginate called Keltone-HV. Another preferred embodiment of the microstructure material is calcium cross-linked alginate or any other alginic acid preparation which provides a hydrocolloid gel of alginic acid suitable for the cell transport and culturing tissue at hand.

In former constructs such as U.S. Pat. No. 5,133,755, the preferred microstructure was hyaluronan which is synonymous with hyaluronic acid, hyaluronate, HA and HY. The hyaluronan was distributed uniformly throughout the internal void volume of the device. According to the teachings of the present invention, an option is provided of selecting whether or not the microstructure should be dispersed throughout all the void spaces depending on whether the arrangement is beneficial to the tissues being treated. The present invention permits incomplete dispersal as desired or complete dispersal throughout the entire void volume of the device but expressing concentration gradients of microstructure material as a means of controlling transplanted cell population numbers within the device's internal domains.

The microstructure approach can carry biologic modifiers with 1) the biodegradable polymeric macrostructure, 2) the microstructure protein, or 3) the microstructure polysaccharide.

This multiple-carrying capacity provides for five different types of locations within the device for loading biologic modifiers: 1) joined at the polymeric macrostructure interior surface; 2) joined to the chemotactic ground substance at the microstructure's exterior surface; 3) located between the biodegradable polymer and the chemotactic ground substance; 4) carried within the chemotactic ground substance in the microstructure interior; and 5) entrapped within the hydration domains of the hyaluronic acid or alginic acid microstructure yet detached from the hyaluronan/alginate polysaccharide.

At the fifth location, the biologic modifier(s) are captured by the hydration domains of the polysaccharide microstructure while the biologic modifiers are still dissolved in their original water solution. The biologically active agent(s) is attached to the hyaluronic acid or alginic acid microstructure but is not in physical contact with the polysaccharide, since it is still dissolved in water which, in turn, is entrapped within the hydration domains of the hyaluronan. This method of delivering biologically active cargo to a tissue defect is impossible with the coating approach of U.S. Pat. No. 5,041,138.

A dry filamentous velour of chemotactic ground substance, specifically RGD attachment moiety of fibronectin carried by hyaluronic acid or alginic acid velour, can be established within the void spaces of the device. Upon saturation with water, water-based cell culture media or fluid blood, the dry velour of chemotactic ground substance is dissolved into a highly viscous gel which maintains the chemotactic ground substance as a network of dissolved polysaccharide strands, still suspended within the void volume of the polymeric macrostructure.

If the cell culture media is a fluid which saturates the device and creates the gel, then those cells suspended in the culture medium will be temporarily trapped within the gel due to the gel viscosity. The degree of gel viscosity and the length of time the gel maintains significantly high viscosities are determined by: 1) the initial molecular weight of the microstructure; 2) the microstructure in vivo rate of degradation; 3) the availability of interstitial fluid to dilute remaining microstructure and remove microstructure degradation products from the region; and 4) the initial concentration of microstructure originally placed within the macrostructure(s) interstices.

Temporarily restraining transported parenchymal cells by means of microstructure gel gives the cells time to execute two critical biologic processes. The first biologic process is the union with the microstructure via direct interaction between the microstructure and the plasma membrane CD44H receptor of the cells as well as union with the RGD attachment moiety of fibronectin which may be incorporated with the microstructure. The second biological process involves bonding with any other biologic modifiers which may be also incorporated with the microstructure or dissolved in water trapped by hydration domains of microstructure polysaccharide.

After approximately 12-to-72 hours in vivo, the microstructure gel has been reduced in viscosity to such an extent that its contents of the microstructure, which now has a reduced molecular weight, together with the surviving cell population attached to the microstructure directly or via RGD attachment moiety of fibronectin, are compelled to rest upon the structural surfaces supplied by the macrostructure polymer.

The volume of space once occupied by the microstructure gel is now occupied by the interstitial fluid and increased numbers of parenchymal cells generated by mitosis of the transplanted parent cells. In the articular cartilage regeneration of the most preferred form, it is desired to protect the transplanted cells from access to fluid blood and collateral circulation. Therefore, blood products will not be found in the void spaces of the cartilage region. In other tissue regeneration situations, however, it is desirable to attract fluid blood into the device's interstices as quickly as possible. In these situations, therefore, fibrin (i.e. blood clot), endothelial budding and granulation tissue advancing within the device interstices from sources of viable collateral circulation will be substances found within the internal void spaces of the device along with the other materials noted above.

The device interaction with cell receptors is an important advantage to the microstructure approach for achieving cell transfer. The biologic processes of cell transfer involved in U.S. Pat. No. 5,133,755 are all mediated by the interaction of various proteins and polysaccharides with specific receptors located in the plasma membrane or "cell wall" of subject cells. These specific receptors are also composed of protein.

Transplanted cells attach to the microstructure and to the RGD attachment moiety of fibronectin supported by the microstructure via interactions of the transplanted cell specific protein receptors located in their cell plasma membranes with the specific amino acid sequences or amine groups of the microstructure complex. For example, there are interactions between the transported cell receptors and the RGD attachment moiety. Another example is the direct interaction of a transported cell membrane receptor such as CD44H and hyaluronan microstructure. Still another example is the interaction of the transported cell membrane receptor and alginate microstructure.

By directly attaching transplanted cells to the three-dimensional microstructure immediately after the cells have been exposed to the transport device, the following results are obtained until the microstructure's viscosity is reduced below a critical level: 1) preserves the three-dimensional configuration of the cell; 2) preserves the entire surface area of each cell in optimum condition for interaction with the microstructure and its cargo of biologically active agents; 3) coats each cell with microstructure material which, in the case of hyaluronan, composes a high percentage of naturally occurring extracellular matrix; 4) maintains the cells, free, in a semi-fluid environment so that they can move in order to establish multiple regions of optimum cell density; 5) maintains the cells in a close proximity to high concentrations of free, solubilized and unattached biologically active agents; and 6) maintains the cargo of biologically active, therapeutic proteins carried in the hydration domains of the microstructure polysaccharide with their three-dimensional configurations undisturbed, thus optimizing their biologic activities.

In cell transplantation, the use of only a chemotactic ground substance coated on a polymeric structure can help many transplanted cells survive. However, as a result of being attached to the unyielding macrostructure surfaces, transplanted cells so attached may have distorted three-dimensional configurations and their plasma membranes may have a reduced surface area available for interaction with biologically active agents.

The present invention departs from prior practice by strategically positioning the microstructure material in that specific portion of the device which performs particular functions unique to the mature anatomy being regenerated in that vicinity. Such segregation of microstructure material within the device is based on the need to endow one portion of the device with special biologic functions that must be isolated from the remainder of the implanted device.

In a more preferred embodiment of the present invention, the microstructure has a primary purpose to deliver chondrocytes only to the cartilage region of the device and support their life function in the mammal's cartilage defect by sequestering the chondrocyte cell population together with the in vitro cell culture medium within its alginate gel. The microstructure has a secondary purpose to present enough chondrocytes to the subchondral bone region immediately adjacent to the cartilage region to insure that a competent osteo-chondral bond is established between the newly developed cartilage and the newly developed bone.

Within the inventive concept of the present invention is the establishment of variations in the concentration of microstructure within the void space network of the macrostructure in order to assure that the therapeutic elements brought from in vitro culture are present within the final device in greatest quantity where they are most needed. Examples of biologically active agents, also known as therapeutic elements and brought in from in vitro culture are cell populations, growth factors, morphogens, other therapeutic agents, drugs, etc. Such variations in concentration can be accomplished by varying concentrations of microstructure solutions prior to investment into macrostructure voids of the device or regions thereof before joining.

Figure 6:
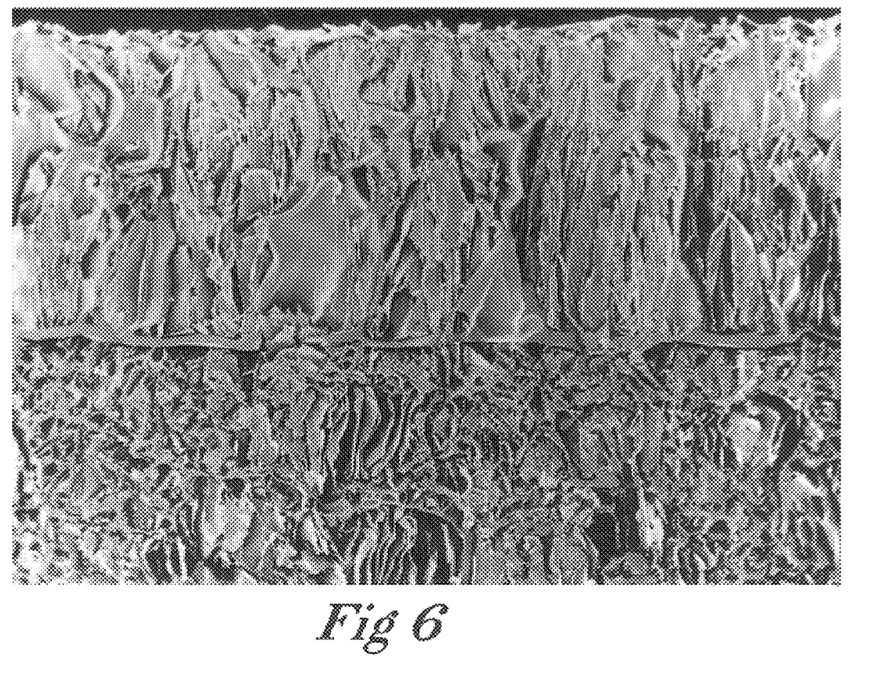
FIG. 6 is a cross-sectional view through the entire device invested with alginate microstructure.

In the more preferred embodiment of the present invention, the alginate velour is present in highest concentration within the tangential zone of the cartilage region and the immediately adjacent locales of the radial zone. The concentration of alginate microstructure declines from the point of highest concentration toward the interface of the radial zone with the subchondral bone region. Microstructure alginate velour is present in the least concentration in the 500 to 800 micrometer thick space of the subchondral bone region.

Within the inventive concept of the present invention is the placing of two or more microstructure materials at strategic locations within the same bioresorbable implant to perform multiple and varied biologic functions segregated to specific anatomic locales of the implant device. For example, a large osteochondral defect would require hyaluronan velour for microstructure in the subchondral region intended for osteoneogenesis. In contrast, alginate velour would be more appropriate microstructure material for the cartilage region of the device intended for chondroneogenesis. The placement of different microstructure material can be accomplished by investing the microstructure material into the regions before they are joined, by investing the device or regions thereof before joining from a first surface with a desired volume of microstructure material less than the total void volume of the macrostructure and then investing from the opposite surface with a volume of a different microstructure material equal to the balance of void volume of the macrostructure.

Figure 7:
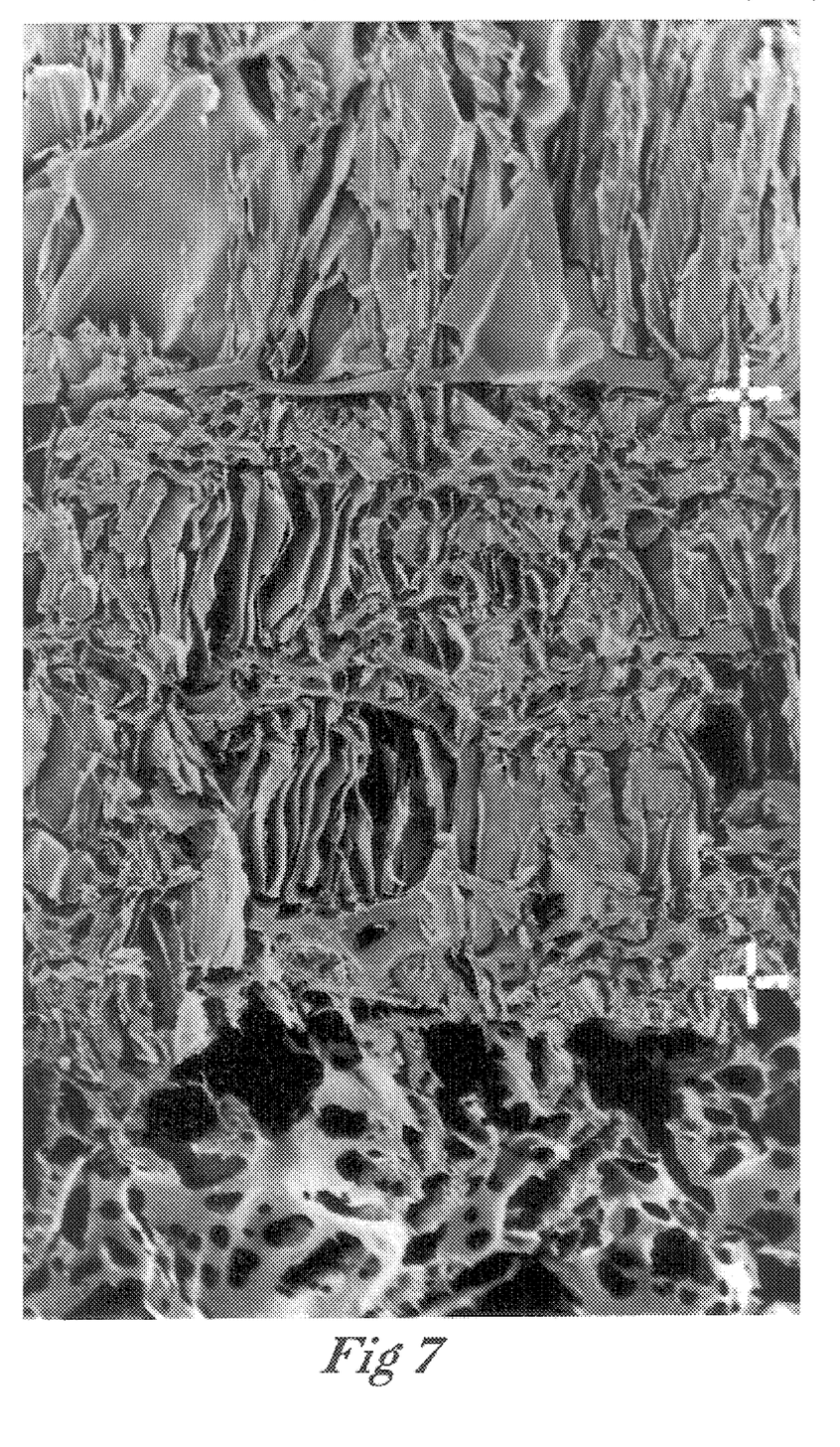
FIG. 7 is a cross-sectional view through the entire device showing a hydrophobic barrier.

Except for the critical location at the interface between the cartilage region, the polymer of the subchondral bone region is hydrophilic by virtue of being treated with a wetting agent such as set forth in U.S. Pat. No. 4,186,448. Beginning at about 500 to 800 micrometers from the interface surface and extending to the interface surface, the macrostructure polymer of the subchondral bone region has been rendered hydrophobic such as by treating the entire device or the subchondral bone region with a surfactant and then inactivating the surfactant on the hydrophobic barrier surfaces or by not treating the barrier surfaces with a surfactant while the remaining portions are treated. Likewise, a hydrophobic barrier may be created within a device of simple (i.e. single) or complex (i.e. multiple) internal architectures by means other than selective treatment of certain polymer regions with a surfactant. For example, a separate fibrillar construct of bioresorbable polymer may be fabricated devoid of surfactant and may be interspersed between two segments of a device whose polymers have been rendered hydrophilic.

Water-based fluids, specifically fluid blood, brought to this locale by capillary action through hydrophilic polymer of the subchondral bone region closest to subchondral bone, are prohibited from traveling further toward the cartilage region by the hydrophobic polymer of the subchondral bone region in this vicinity. The interstices of the hydrophobic fibrillar membrane would eventually accommodate cell growth, but the immediate effect of such a membrane would be to prevent passage of water-based fluids across its boundaries.

The hydrophobic barrier is a significant advance and development of devices intended for use in chondroneogenesis because hyaline cartilage, specifically the articular cartilage of joints, is an avascular tissue and must be protected from intimate contact with sources of high oxygen tension such as blood. When the recipient cartilage tissue defect is prepared to receive the implant, it is necessary to continue the defect into the underlying subchondral bone, called the cancellous bone, to assure that there will be a new bone formed beneath the cartilage region which will produce a competent bond with the newly developing cartilage.

Such tissue preparation engages the rich collateral circulation of subchondral cancellous bone and its associated bone marrow. If the cultured chondrocytes and specifically the cartilage cells come into contact with the fluid blood produced by this source of collateral circulation, they will fail to maintain their chondrocyte phenotype.

It is essential that the majority of cultured chondrocytes be protected from intimate contact with collateral circulation so that they will retain their chondrocyte phenotype and continue to produce collagen Type II in the architectural pattern dictated by the macrostructure polymer of the cartilage region. The hydrophobic barrier of the preferred form of the present invention described above achieves this objective.

It can then be appreciated that the anatomically specific bioresorbable device according to the teachings of the present invention has a fabricated macrostructure closely resembling the mature tissues which are to be regenerated by the completed implant. Further, the anatomically specific bioresorbable device of the present invention integrates the macrostructure, microstructure, cells cultured in vitro, culture medium and associated growth factors, morphogens, drugs and other therapeutic agents.

According to the preferred teachings of the present invention, the anatomically specific bioresorbable device according to the preferred teachings of the present invention can be utilized as a transport system for chondrocytes, growth factors, morphogens and other biologically active agents, in treatment of articular cartilage defects. In particular and in the preferred form, suitable source tissue is harvested and the cells are cultured using standard chondrocyte culturing methods, with the specific cell type in the most preferred form being articular cartilage chondrocyte. The cartilage defect is surgically prepared by removing diseased or damaged cartilage to create a cartilage and subchondral bone defect, with the defect extending approximately 0.5 cm to 1.0 cm into subchondral cancellous bone. With the device and defect having generally the same shape, the device is inserted into the tissue defect such as by press fitting. A volume of in vitro cell culture suspension is measured out by a microliter syringe which generally matches exactly the void volume of the cartilage region macrostructure invested by the microstructure and is injected onto the outer surface of the tangential zone of the cartilage region and which will ultimately be in contact with synovial fluid. The joint anatomy can then be replaced in proper position and the wound can be closed.

Although the preferred form relates to the transport and in vivo culturing of chondrocytes, it should be noted that the teachings of the present invention, and the useful. devices fabricated as a result thereof, are intended to transport, and sustain in life, any cell type having therapeutic value to animals and plants. Examples of other cells of therapeutic value other than chondrocytes are: islets of Langerhans which produce insulin, liver parenchymal cells which have the capacity to regenerate liver tissue, and tumor cells used to stimulate the immune system against a certain tumor type.

Thus since the invention disclosed herein may be embodied in other specific forms without departing from the spirit or general characteristics thereof, some of which forms have been indicated, the embodiments described herein are to be considered in all respects illustrative and not restrictive. The scope of the invention is to be indicated by the appended claims, rather than by the foregoing description, and all changes which come within the meaning and range of equivalency of the claims are intended to be embraced therein.

What is claimed is:

1. An anatomically specific device for regenerating at least first and second, juxtaposed tissues having different histologic patterns, prior to implantation, comprising, in combination: a first region having an internal three-dimensional architecture to approximate the histologic pattern of the first tissue; and a second region having an internal three-dimensional architecture to approximate the histologic pattern of the second tissue, with the first and second regions being integrally connected together at an interface without the use of solvents or chemical reactions between the first and second regions, with the regions being formed of a bioresorbable polymer.

2. The anatomically specific device of claim 1 wherein each of the first and second regions include a macrostructure defining void spaces, with the device further comprising, in combination: at least a first material for enhancing the attachment of cells to the three-dimensional architecture in the void spaces of at least one of the first and second regions.

3. The anatomically specific device of claim 2 wherein the cell attachment enhancing material is present at varying concentrations in the regions.

4. The anatomically specific device of claim 2 further comprising, in combination: a second material for enhancing the attachment of cells to the three-dimensional architecture in the void spaces of the second region with the first region being substantially free of the second cell attachment enhancing material, with the first cell attachment enhancing material located in the void spaces of the first region and the second region being substantially free of the first cell attachment enhancing material.

5. The anatomically specific device of claim 1 wherein the first region is divided into first and second zones having differing three-dimensional patterns, with the second zone located between the first zone and the second region.

6. The anatomically specific device of claim 5 wherein the three-dimensional pattern of the first zone includes a network of intercommunicating voids which have an orientation parallel to the interface surface, and the three-dimensional pattern of the second zone includes a network of inter-communicating voids extending between the first zone and the second region.

7. The anatomically specific device of claim 6 further comprising, in combination: a porous microstructure formed from a material for enhancing the attachment of cells to the three-dimensional architecture and located in the intercommunication voids of the first region and carried by and separate from the bioresorbable polymer forming the first region.

8. The anatomically specific device of claim 7 wherein the cell attachment enhancing material is alginate.

9. The anatomically specific device of claim 8 wherein the first tissue is cartilage and the second tissue is subchondral cancellous bone; and wherein the device further comprises, in combination: RGD attachment moiety of fibronectin carried by the cell attachment enhancing material and within the intercommunicating voids of the first region.

10. The anatomically specific device of claim 9 wherein the second region includes a porous macrostructure including interconnecting voids; and wherein the device includes a material for enhancing the attachment of cells to the three-dimensional architecture located in the interconnecting voids of the porous macrostructure and carried by and separate from the bioresorbable polymer forming the porous macrostructure.

11. The anatomically specific device of claim 10 wherein the cell attachment enhancing material of the porous macrostructure is a chemotactic ground substance in the form of hyaluronic acid.

12. The anatomically specific device of claim 1 wherein the first and second regions include intercommunicating voids; and wherein the device further comprises, in combination: at least one hydrophobic barrier within the three-dimensional architecture of at least one of the first and second regions, with the second region outside of the hydrophobic barrier being hydrophilic.

13. The anatomically specific device of claim 12 wherein the first and second regions are formed by a single bioresorbable polymer, with the single bioresorbable polymer of the first region being hydrophobic and the second region being hydrophilic by treatment with a surfactant.

14. The anatomically specific device of claim 12 wherein the hydrophobic barrier is spaced from the interface surface.

15. The anatomically specific device of claim 14 wherein the hydrophobic barrier begins in the second region about 500 to 800 micrometers from the interface surface.

16. The anatomically specific device of claim 15 wherein the first tissue is cartilage and the second tissue is subchondral cancellous bone.

17. A bioresorbable polymer device for regenerating cartilage tissue interfacing at an interface with subchondral cancellous bone and located between the subchondral cancellous bone and synovial fluid, prior to implantation, comprising, in combination: a tangential zone including a network of intercommunicating void spaces having an orientation parallel to the interface and in communication with the synovial fluid; and a radial zone located between the tangential zone and the interface, with the radial zone including void spaces extending between and providing communication between the interface and the tangential zone.

18. The bioresorbable device of claim 17 wherein the tangential zone includes channels extending parallel to the interface and formed by major polymer strands running parallel to each other, with the channels separated by a network of minor polymer strands extending parallel to the interface and generally perpendicular to the major polymer strands.

19. The bioresorbable device of claim 18 wherein the radial zone includes thin sheets of the bioresorbable polymer arranged perpendicular to the interface.

20. The bioresorbable device of claim 17 further comprising, in combination: a porous microstructure formed from a material for enhancing the attachment of cells to the three-dimensional architecture and located in the void spaces of at least one of the tangential and radial zones and carried by and separate from the bioresorbable polymer defining the void spaces.

21. The bioresorbable device of claim 20 wherein the cell attachment enhancing material is alginate.

22. The bioresorbable device of claim 21 further comprising, in combination: RGD attachment moiety of fibronectin carried by the cell attachment enhancing material and within the void spaces.

23. The bioresorbable device of claim 20 wherein the cell attachment enhancing material is present at varying concentrations in the zones.

24. The bioresorbable device of claim 17 further comprising, in combination: means for protecting the tangential and radial zones from intimate contact with collateral circulation from the subchondral cancellous bone.

25. The bioresorbable device of claim 24 wherein the protecting means comprises a hydrophobic barrier at the interface with the radial zone.

26. A bioresorbable device for facilitating healing of voids in tissue comprising, in combination: a macrostructure made from a polymer providing an internal three-dimensional architecture defining a network of void spaces; and a material for enhancing the attachment of cells to the three-dimensional architecture carried by the macrostructure at varying concentrations in the void spaces of the three-dimensional architecture.

27. The bioresorbable device of claim 26 wherein the macrostructure includes first and second, spaced surfaces, with the concentration of the cell attachment enhancing material carried by the macrostructure decreasing from the first surface to the second surface.

28. The bioresorbable device of claim 27 wherein the cell attachment enhancing material forms a porous microstructure located in the intercornecting voids and carried by and separate from the polymer forming the macrostructure.

29. A bioresorbable device for facilitating healing of voids in tissue, prior to implantation, comprising, in combination: a structure made from a polymer providing an internal three-dimensional architecture including at least first and second locations; and a first material for enhancing the attachment of cells to the three-dimensional architecture carried by the structure in the first location, with the second location being substantially free of the first cell attachment enhancing material.

30. The bioresorbable device of claim 29 further comprising, in combination: a second material for enhancing the attachment of cells to the three-dimensional architecture carried by the structure in the second location, with the first location being substantially free of the second cell attachment enhancing material.

31. The bioresorbable device of claim 30 wherein the first cell attachment enhancing material facilitates osteoneogenesis and the second cell attachment enhancing material facilitates chondroneogenesis.

32. The bioresorbable device of claim 31 wherein the first cell attachment enhancing material comprises a chemotactic ground substance in the form of hyaluronic acid and the second cell attachment enhancing material comprises alginate.

33. The bioresorbable device of claim 31 further comprising, in combination: RGD attachment moiety of fibronectin carried by the second cell attachment enhancing material.

34. The bioresorbable device of claim 33 wherein the structure is in the form of a porous macrostructure including interconnecting voids; and wherein the cell attachment enhancing materials form porous microstructures located in the interconnecting voids of the respective locations and carried by and separate from the polymer forming the porous macrostructure.

35. A bioresorbable device for facilitating healing of voids in tissue, prior to implantation, comprising, in combination: a structure made from a polymer providing an internal three-dimensional architecture approximating a first tissue; and a barrier positioned within the three-dimensional architecture of the structure for prohibiting water-based fluid from passing therethrough; wherein the barrier is hydrophobic and the three-dimensional architecture outside of the barrier is hydrophilic on at least one surface.

36. The bioresorbable device of claim 35 wherein the polymer is hydrophobic and is treated with a surfactant to become hydrophilic.

37. The bioresorbable device of claim 35 wherein the internal three-dimensional architecture approximates a histologic pattern of the first tissue.

38. A method comprising the steps of: providing a structure made from a bioresorbable polymer and having an internal three-dimensional architecture including at least first and second locations; providing a first material for enhancing the attachment of cells to the three-dimensional architecture; and investing the first location with the first cell attachment enhancing material while the second location is substantially free of the first cell attachment enhancing material.

39. The method of claim 38 wherein the providing step comprises the steps of: providing the first location; providing the second location separate from the first location; and joining the first and second locations to form the structure; and wherein the investing step comprises the step of investing the first location with the first cell attachment enhancing material prior to the joining step.

40. The method of claim 39 wherein the structure includes first and second, spaced surfaces, with the first surface located on the first location and the second surface located on the second location; and wherein the investing step comprises investing the first location through the first surface with a volume of the cell attachment enhancing material less than or equal to the volume of cell attachment enhancing material which could be carried by the first location.

41. The method of claim 38 further comprising the steps of: providing a second material for enhancing the attachment of cells to the three-dimensional architecture; and investing the second location with the second cell attachment enhancing material while the first location is substantially free of the second cell attachment enhancing material.

42. A bioresorbable polymer device for regenerating cartilage tissue interfacing at an interface with subchondral cancellous bone and located between the subchondral cancellous bone and synovial fluid, prior to implantation, comprising, in combination: a cartilage region having an internal three-dimensional architecture to approximate the histologic pattern of the cartilage tissue; a subchondral bone region having an internal three-dimensional architecture to approximate the histologic pattern of the subchondral cancellous bone, with the cartilage and subchondral bone regions being integrally connected together at an interface surface, with the regions being formed of a bioresorbable polymer, with the cartilage region being divided into a tangential zone including a network of intercommunicating void spaces having an orientation parallel to the interface surface and in communication with the synovial fluid and a radial zone located between the tangential zone and the interface surface, with the radial zone including void spaces extending between and providing communication between the interface surface and the tangential zone; a material for enhancing the attachment of cells to the three-dimensional architecture at varying concentrations in the cartilage region, with the subchondral bone region being substantially free of the cell attachment enhancing material; and a barrier formed between the cartilage and subchondral bone regions for prohibiting water-based fluid from passing therethrough.

* * * * *

UNITED STATES PATENT AND TRADEMARK OFFICE
CERTIFICATE OF CORRECTION

PATENT NO. : 5,981,825

DATED : November 9, 1999

INVENTOR(S) : John H. Brekke

Page 1 of 2

It is certified that error appears in the above-identified patent and that said Letters Patent is hereby corrected as shown below:

Page 2 of the Cover Page, left column, Other Publications, *Attachment and survival of perichondrocytes in a porous polylactic acid (PLA) matrix* article, cancel "Districk" and substitute therefor -- District --.

Column 2, line 27, after "Structure" add -- . --.

Column 2, line 56, after "Materials" add -- . --.

Column 2, line 65, after "Cell" add -- . --.

Column 18, line 37, after "therethrough.", add the following:

-- 43. A bioresorbable device for facilitating healing of structural voids in bone, cartilage as well as soft tissue comprising, in combination:

a. a porous macrostructure, made from a bioresorbable polymer, providing a porous architecture as well as structural and mechanical integrity to the void being treated, with the porous macrostructure including interconnecting voids; and     b. a porous microstructure, formed from a material for enhancing the attachment of cells to the porous macrostructure and located in the voids and carried by and separate from the

UNITED STATES PATENT AND TRADEMARK OFFICE
CERTIFICATE OF CORRECTION

PATENT NO. : 5,981,825
DATED : November 9, 1999
INVENTOR(S) : John H. Brekke

It is certified that error appears in the above-identified patent and that said Letters Patent is hereby corrected as shown below:

bioresorbable polymer forming the porous macrostructure, with the cell attachment enhancing material being alginate. --.

Signed and Sealed this

Fifteenth Day of May, 2001

Attest:

NICHOLAS P. GODICI

Attesting Officer      Acting Director of the United States Patent and Trademark Office